(12) United States Patent
Bornzin et al.

(10) Patent No.: US 6,377,852 B1
(45) Date of Patent: Apr. 23, 2002

(54) IMPLANATABLE CARDIAC STIMULATION DEVICE AND METHOD FOR PROLONGING ATRIAL REFRACTORINESS

(75) Inventors: Gene A. Bornzin, Simi Valley; Laurence S. Sloman, West Hollywood; Peter Boileau, Valencia; Joseph J. Florio, La Canada, all of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/488,284

(22) Filed: Jan. 20, 2000

(51) Int. Cl.[7] ............................................... A61N 1/362
(52) U.S. Cl. ......................................................... 607/9
(58) Field of Search .............................. 607/4, 5, 14, 9

(56) References Cited

U.S. PATENT DOCUMENTS

| 4,674,509 A | 6/1987 | DeCote, Jr. | |
| 5,403,356 A | 4/1995 | Hill et al. | 607/14 |
| 5,476,483 A | 12/1995 | Bornzin et al. | 607/17 |
| 5,476,487 A | 12/1995 | Sholder | 607/28 |
| 5,683,429 A | 11/1997 | Mehra | 602/14 |

*Primary Examiner*—Scott M. Getzow

(57) ABSTRACT

An implantable cardiac stimulation device, e.g., a pacemaker or an implantable cardioverter defibrillator (ICD), is provided which prolongs the atrial refractoriness of a heart. The implantable cardiac stimulation device includes a generator that delivers pacing pulses to an atrium of a heart and a detector that detects atrial activations of the heart. An inhibitor is coupled to the detector that inhibits the generator when an atrial activation is detected within an escape interval. A generator control coupled to the generator causes the generator to deliver a primary pacing pulse to the atrium at the end of the escape interval, absent an atrial activation being detected within the escape interval, and causes the generator to deliver a secondary pacing pulse to the atrium a delay time after an atrial activation is detected within the escape interval or the delivery of a primary pacing pulse to the atrium.

49 Claims, 4 Drawing Sheets

IMPLANATABLE CARDIAC STIMULATION DEVICE AND METHOD FOR PROLONGING ATRIAL REFRACTORINESS

BACKGROUND OF THE INVENTION

The present invention generally relates to implantable cardiac stimulation devices, e.g., pacemakers or implantable cardioverter defibrillators (ICDs). The present invention more particularly relates to an implantable cardiac stimulation device and method which provide pacing of a heart in different modalities while assisting in the treatment of atrial arrhythmias by prolonging atrial refractoriness of the heart.

BACKGROUND OF THE INVENTION

Atrial arrhythmias such as paroxysmal atrial fibrillation and flutter are very common arrhythmias. Such arrhythmias are present in a large percentage of the bradycardia pacemaker patient population. For these patients, pacemaker therapy could become a primary indication for treatment of the disorder.

The prolongation of atrial refractoriness is known to reduce the likelihood of atrial arrhythmias in some patients. Certain drugs, such as amiodarone or beta-blockers, like sotalol, help to maintain sinus rhythm by prolonging atrial refractoriness and thus act to reduce atrial arrhythmias in some patients. Other drugs help slow the ventricular rate once atrial fibrillation has occurred. These drugs reduce ventricular rate by AV nodal inhibition. These include verapamil, diltiazem, beta-blockers, and/or digoxin. However, drugs can cause side effects and many patients are resistant to drug therapy.

It would therefore be desirable to have some means other than the ingestion of drugs available to this patient population for prolonging atrial refractoriness. To that end, preemptive electrical stimulation of the atrium is known to prevent atrial arrhythmias in some patients. The present invention addresses these issues in the form of an implantable cardiac stimulation device capable of pacing the heart of a patient in single or dual chamber modalities while pacing the atria in an improved manner which assists in prolonging atrial refractoriness and treating atrial arrhythmias. Furthermore, the present invention provides therapeutic benefit to patients with hypertension, heart failure, acute myocardial infarction and other disorders as described below.

Others have sought to prevent the onset of atrial arrhythmias with pacing. For example, U.S. Pat. No. 5,403,356 to Hill uses at least two electrode pairs with one electrode pair being used to detect a depolarization at a one site, e.g., the high right atrium and detection triggers stimulation to the triangle of Koch or a site of prolonged effective refractory period. The triggered stimulation occurs synchronous with the detection or following a short time delay of less than 50 ms. This short time delay is used to prevent stimulation during the vulnerable period in the atrium and thus avoids precipitating atrial arrhythmias. Although stimulation at the triangle of Koch is intended to synchronize the atrium and the refractory periods in the atrium, it is not intended to act to prolong atrial refractory periods. Furthermore, this approach requires implantation of multiple atrial leads and thus complicates the process of administering therapy.

Atrial tachyarrhythmias are often preceded by at least one atrial premature beat that spontaneously originates from an ectopic site in the atrium. Mehra has proposed in U.S. Pat. No. 5,683,429 using burst pacing at multiple sites immediately after an atrial premature beat to prevent a reentry event precipitated by the atrial premature beat. Mehra also teaches that there may be an unspecified time delay between the atrial premature beat and the burst of pacing. Although this algorithm was intended to block reentry as a result of atrial premature beats, it does not act to prevent atrial premature beats and the potentially ensuing atrial arrhythmias.

The present invention further acts to prevent atrial premature beats by making the ectopic foci responsible for the atrial premature beat refractory and thus incapable of spontaneously depolarizing.

Furthermore, the present invention has the effect of prolonging the interval between the pacing atrial events and succeeding spontaneous native atrial depolarizations. This actually makes it possible to reduce the hemodynamically effective cardiac rate to a rate lower than the native rate which is useful for regulating blood pressure. This will benefit patients with essential hypertension, and patients with heart failure in whom reducing blood pressure reduces cardiac work and reduces ventricular wall tension. Reducing the ventricular wall tension allows the heart to assume a smaller more normal geometry and thus allows for more effective contraction.

Slowing the hemodynamically effective rate below the native rate has significant benefits to patients with coronary heart disease. Perfusion of the myocardium takes place during diastole and thus slowing the rate increases the diastolic interval and thus allows more time for perfusion of ischemic cardiac tissue.

A further therapeutic application of the present invention is in the treatment of patients with diastolic dysfunction. These patients have hypertrophied hearts with reduced compliance. Reducing the effective hemodynamic rate has the benefit of allowing more time for filling the relatively stiff, incompliant ventricles and thus enhances stroke volume and cardiac performance.

Other therapeutic benefits are likely to become apparent with extensive practice of the present invention.

SUMMARY OF THE INVENTION

The invention therefore provides an implantable cardiac stimulation device, e.g., a pacemaker or ICD, including generating means for delivering pacing pulses to an atrium of a heart and control means coupled to the generating means for causing the generating means to deliver a primary pacing pulse to the atrium and causing the generating means to deliver a secondary pacing pulse to the atrium a delay time after the delivery of the primary pacing pulse.

In accordance with further aspects of the present invention, the implantable cardiac stimulation device may further include a detector that detects atrial activations of the heart, wherein the generator control inhibits the generator from providing the primary pacing pulse when an atrial activation is detected during an escape interval and wherein the generator control further causes the generator to deliver the secondary pacing pulse to the atrium the delay time after an atrial activation is detected during the escape interval.

In accordance with still further aspects of the present invention, the implantable cardiac stimulation device may further include an AV delay timer that times an AV delay interval responsive to the delivery of a primary pacing pulse or the detection of an atrial activation within the escape interval, and a second generator responsive to the AV delay timer that provides a ventricular pacing pulse at the end of the AV delay interval.

In accordance with still further aspects of the present invention, the implantable cardiac stimulation device may further include a ventricular detector that detects ventricular activations of the heart and a ventricular inhibitor that inhibits the second generator when a ventricular activation is detected during the AV delay interval.

The present invention still further provides a method of pacing atria of a heart. The method includes the steps of delivering a primary pacing pulse to one of the atria of the heart, timing a delay time period following the delivery of the primary pacing pulse, and delivering a secondary pacing pulse to the one of the atria at the end of the delay time period.

The present invention also discloses a means to automatically establish the delay timing of delivery of the secondary atrial pulse. The advantage of automated adjustment of the delivery of the secondary pacing pulse is that there is no necessity to manually adjust the interval. Additionally, if there are physiologic changes to the patients heart that would necessitate adjustment of the delay it will be automatically performed by the device thus automatically optimizing therapy.

The novel features of the invention are set forth with particularity in the appended claims. The invention will be best understood from the following description when read in conjunction with the accompanying drawings.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference characters identify identical elements, and wherein:

DETAILED DESCRIPTION OF THE PREFERRED EMBODIMENTS

Figure 1:
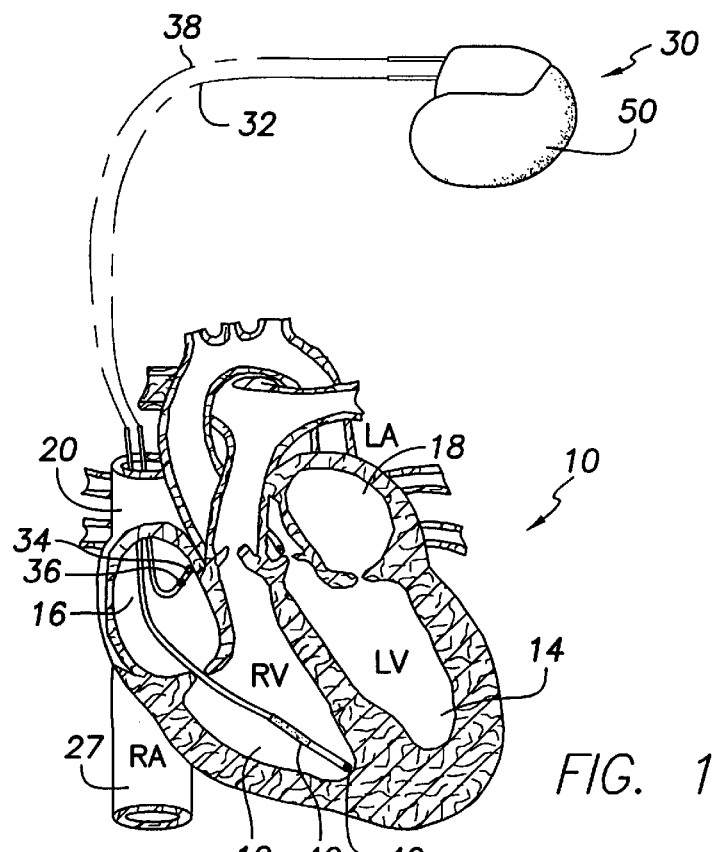
FIG. 1 is a schematic illustration of a human heart, in need of cardiac rhythm management, shown in association with an implantable pacemaker embodying the present invention.

Referring now to FIG. 1, a heart 10 in need of cardiac rhythm management and an associated implantable pacemaker 30 embodying the present invention are shown. The portions of the heart 10 illustrated in FIG. 1 are the right ventricle 12, the left ventricle 14, the right atrium 16 and the left atrium 18. Also illustrated are the superior vena cava 20 and inferior vena cava 27. As is well known in the art, the pacemaker 30 is arranged to be implanted in an upper left chest portion of a patient within a subcutaneous pocket.

The pacemaker 30 includes a first endocardial lead 32 preferably having an electrode pair including a distal electrode 34 and a proximal electrode 36 implanted in electrical contact with an atrium of the patient's heart. The electrodes 34 and 36 are implanted in the right atrium 16 to support sensing of right atrial electrical activity and delivery of pacing pulses to the right atrium 16.

Similarly, a second endocardial lead 38 preferably has an electrode pair including a distal electrode 40 and a proximal electrode 42 implanted in electrical contact with a ventricle of the patient's heart. The electrodes 40 and 42 are implanted in the right ventricle 12 to support sensing of right ventricular electrical activity and delivery of pacing pulses to the right ventricle 12.

Figure 2:
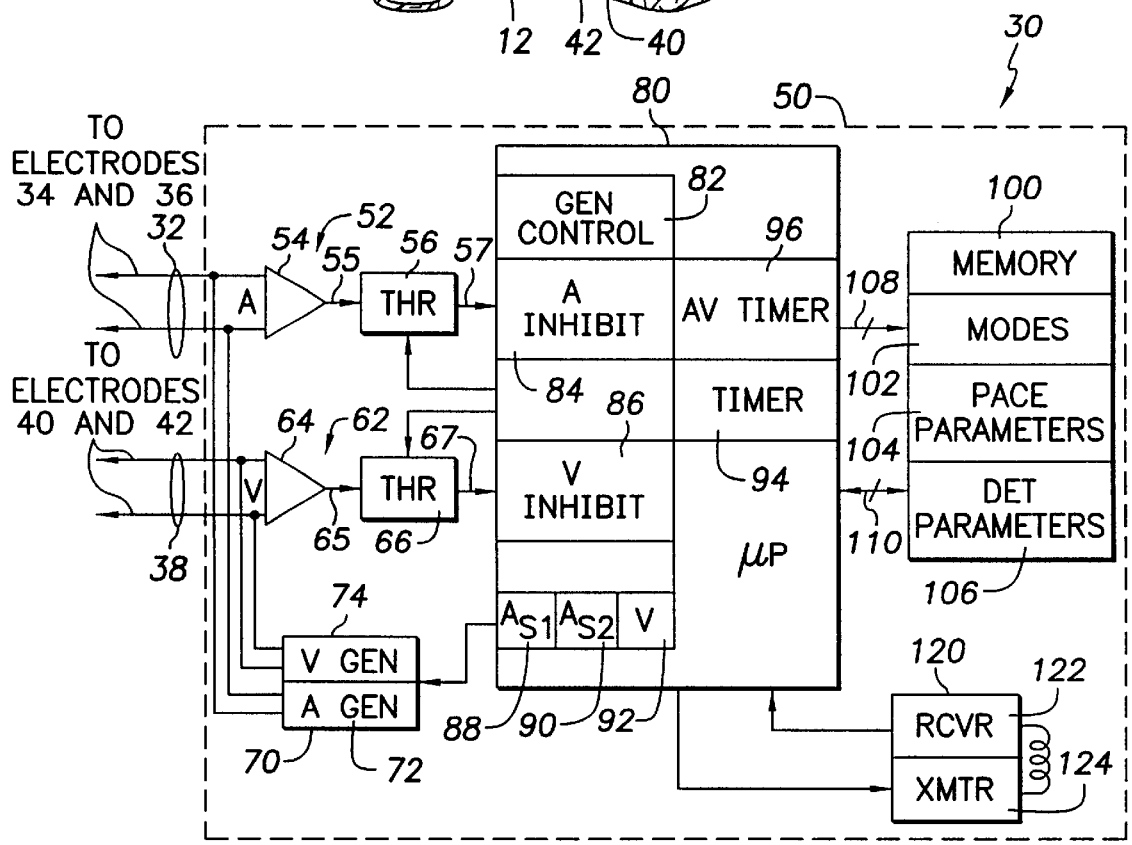
FIG. 2 is a block diagram of the implantable pacemaker of FIG. 1.

The implantable pacemaker 30 includes a hermetically sealed, electrically conductive enclosure 50. As illustrated in FIG. 2, the pacemaker 30 includes within the enclosure 50 an atrial sense channel 52, a ventricular sense channel 62, and a pacing pulse generator 70 including a first or atrial pulse generator 72 (A Gen) for providing atrial pacing pulses and a second or ventricular pulse generator 74 (V Gen) for providing ventricular pacing pulses. The pacemaker 30 further includes a control circuit 80, preferably a microprocessor, a memory 100 and a telemetry stage 120.

The atrial sense channel 52 includes an atrial sense amplifier 54 and an atrial threshold detector 56. The atrial sense amplifier 54 has inputs coupled to electrodes 34 and 36 of lead 32 and generates an output signal 55 which is input to the atrial threshold detector 56. As further illustrated the atrial threshold detector 56 has an output 57 which is coupled to the microprocessor 80.

The atrial sense amplifier 54, together with electrodes 34 and 36 sense electrical activity in the right atrium 16. When the output 55 from the atrial sense amplifier 54 transitions through a programmed threshold of the atrial threshold detector 56, the atrial threshold detector 56 provides input signal 57 to the microprocessor 80 indicating that an atrial activation or P-wave has been detected. Such detection is well known in the art.

Similarly, the ventricular sense channel 62 includes a ventricular sense amplifier 64 and a ventricular threshold detector 66. The ventricular sense amplifier 64 has inputs coupled to the electrodes 40 and 42 of lead 38 and generates an output signal 65 which is input to the ventricular threshold detector 66. As further illustrated, the ventricular threshold detector 66 has an output 67 which is coupled to the microprocessor 80.

The ventricular sense amplifier 64, together with electrodes 40 and 42 sense electrical activity in the right ventricle 12. When the output 65 of the ventricular sense amplifier 64 transitions through a programmed threshold of the ventricular threshold detector 66, the ventricular threshold detector 66 provides an input signal 67 to the microprocessor 80 indicating that a ventricular activation or R-wave has been detected. Such detection is also well known in the art.

The first, or atrial pulse generator 72 has outputs coupled to electrodes 34 and 36 through lead 32. This permits pacing pulses produced by the atrial pulse generator 72 to be applied to the right atrium 16. As will be seen hereinafter, these pacing pulses include primary atrial pacing stimulation pulses ($A_{S1}$) and secondary atrial pacing stimulation pulses ($A_{S2}$).

The second or ventricular pulse generator 74 has outputs coupled to electrodes 40 and 42 through lead 38. This permits pacing pulses produced by the ventricular pulse generator 74 to be applied to the right ventricle 12.

The sense channels 52 and 62 and pulse generators 72 and 74 permit the pacemaker 30, in accordance with the present invention, to provide single chamber atrial pacing or combined dual chamber atrial and ventricular pacing. The overall functioning of the pacemaker 30 is controlled by the microprocessor 80.

The microprocessor 80 implements selected pacing modalities by executing operating instructions stored in the memory 100, and more specifically, in a memory portion 102. In executing the instructions stored in memory portion 102, the microprocessor 80 further utilizes pacing parameters stored in memory portion 104 and detection parameters stored in memory portion 106. The pacing parameters may include, for example, AV delays, atrial and ventricular pacing energies, atrial and ventricular escape intervals, and basic rates, etc. The detection parameters may include, for example, blanking period durations, refractory periods, and detection thresholds for the threshold detectors 56 and 66. Such pacing parameters and detection parameters are well known in the art.

The telemetry stage 120 permits mode selections and storage of pacing and detection parameters in the memory 100 to be made through the use of an external programmer (not shown) of the type well known in the art. The telemetry stage includes a receiver 122 which receives telemetry commands including mode selection commands and pacing and detection parameters from the programmer. The receiver 122 conveys the commands to the microprocessor 80 which then stores them in memory 100.

The telemetry stage 120 also includes a transmitter 124. The transmitter may be used for transmitting data to the programmer. The transmitted data may include sensed electrograms or status information, for example, as is well known in the art.

The microprocessor 80 is coupled to the memory 100 by a multiple-bit address bus 108 and a bidirectional, multiple-bit data bus 110. The microprocessor 80 uses the address bus 108 to fetch operating instructions or programmable parameters from the memory at address locations defined on the address bus 108. The fetched instructions and parameters are conveyed to the microprocessor 80 over the data bus 110. Similarly, the microprocessor 80 may store data in the memory 100 at memory locations defined on the address bus 108. The microprocessor 80 conveys the data to the memory over the data bus 110. Such microprocessor and memory operations are conventional in the art.

When executing the operating instructions stored in memory 100, the microprocessor 80 implements a number of functional stages in accordance with the present invention. Those stages include a generator control stage 82 which includes an atrial generator inhibiting stage 84, a ventricular generator inhibiting stage 86, a primary atrial pacing pulse stimulation control 88 ($A_{S1}$), a secondary atrial pacing pulse stimulation control 90 ($A_{S2}$), and a ventricular pacing pulse stimulation control 92 (V). The stages of microprocessor 80 further include an atrial delay timer 94 and an AV delay timer 96.

In accordance with a primary aspect of the present invention, whether the pacemaker 30 is in a single or dual chamber pacing modality, the generator control stage 82 causes the atrial pulse generator 72 to provide a secondary atrial pacing pulse to the right atrium 16 a secondary pacing pulse delay time after causing the atrial pulse generator 72 to provide a primary atrial pacing pulse to the right atrium 16. When atrial pacing is in a demand mode, the generator control stage 82 inhibits the atrial pulse generator 72, and thus the delivery of the primary pacing pulse if an atrial event, i.e., depolarization signifying activation of the atrium, is detected during an atrial escape interval. However, the generator control stage 82 still causes the atrial pulse generator 72 to deliver the secondary pulse after the secondary pacing pulse delay time following detection of the atrial event. The secondary pacing pulse prolongs the refractoriness of the atria. The secondary pacing pulse delay time period, i.e., the period of time between the primary atrial pacing pulse or the detected atrial depolarization and the secondary atrial pacing pulse, is preferably between about 180 to 300 milliseconds. The atrial refractory period is typically about 130 milliseconds in normal patients but may be as short as 80 milliseconds in some patients with recurrent atrial arrhythmias. Accordingly, the secondary pacing pulse will serve to prolong the period during which the atria are refractory and thus decrease the likelihood of a spontaneous reentrant arrhythmia. The ventricle and the AV node will be refractory when the secondary atrial pacing pulse is delivered. As a result, the secondary atrial pulse will have no affect on the ventricle. Atrial kick will be provided by the primary depolarization and it is likely that the atria will be in hemodynamic block. Thus, the hemodynamics will not be disturbed by the secondary atrial pacing pulse.

As previously mentioned, the atrial pacing may be in a demand mode. To that end, the atrial generator inhibiting stage 84 preferably includes an atrial delay timer 94 for timing an atrial escape interval. If, during the atrial escape interval, the atrial sense channel 52 detects an atrial event, the atrial generator inhibiting stage 84 will preclude the primary atrial pulse stimulation control 88 from issuing a control signal to the atrial pulse generator 72 and thus will inhibit delivery of the primary pacing pulse. However, upon detection of an atrial event by the atrial sense channel 52, the atrial delay timer 94 begins timing the secondary pacing pulse delay period. At the end of the secondary pacing pulse delay time period, the secondary atrial pacing pulse stimulation control 90 issues a control signal to the atrial pulse generator 72 to cause it to provide the secondary pacing pulse.

If an atrial event is not detected by the atrial sense channel 52 during the atrial escape interval, the primary atrial pacing pulse stimulation control 88 issues a control signal to the atrial pulse generator 72 at the end of the atrial escape interval to cause it to provide the primary pacing pulse. When the primary pacing pulse is provided by atrial pulse generator 72, the atrial delay timer 94 commences to time the secondary pacing pulse delay time period. At the end of the secondary pacing pulse delay time, the secondary atrial pacing pulse stimulation control 90 then issues a control signal to the atrial pulse generator 72 to cause the generator 72 to provide the secondary pacing pulse.

The atrial pacing described above may be provided in a single chamber atrial pacing modality. In such a modality, the primary pacing pulses, absent spontaneous atrial activations, will occur at a basic rate consistent with a basic pacing rate stored in memory portion 104 of memory 100. However, the atrial pacing may be provided in association with ventricular pacing as well.

When dual chamber pacing is provided, the provision of a primary atrial pacing pulse or the detection of an atrial activation during the atrial escape interval causes the AV delay timer 96 to time an AV delay time period. At the end of the AV delay time period, the ventricular pacing pulse stimulation control 92 issues a control signal to the ventricular pulse generator 74 causing it to provide a ventricular pacing pulse to the right ventricle 12. Additionally, the ventricular pacing may further be in a demand mode. To that end, if a ventricular activation is detected by the ventricular sense channel 62 during the AV delay time period timed by the AV delay timer 96, the ventricular inhibit stage 86 will preclude the ventricular pacing pulse stimulation control 92 from issuing its control signal to the ventricular generator 74 and thus inhibiting the delivery of the ventricular pacing pulse.

In view of the foregoing, it may be seen that the present invention provides an implantable pacemaker which extends the atrial refractory period of a patient's heart without the use of drug therapy. The secondary atrial pacing pulse follows either a spontaneous atrial activation or a primary atrial pacing pulse by a predetermined time period, typically between 180 to 300 milliseconds. This timing will not disturb the hemodynamics of the heart. The secondary atrial pacing pulse may slow the sinus rate of the heart, thus increasing the likelihood of dynamic atrial overdrive pacing wherein overdriving the intrinsic atrial rhythm may occur. Lastly, the second atrial stimulus will not be conducted because the ventricle and AV node will be refractory due to a conducted ventricular depolarization or because of a paced ventricular depolarization.

Figure 3:
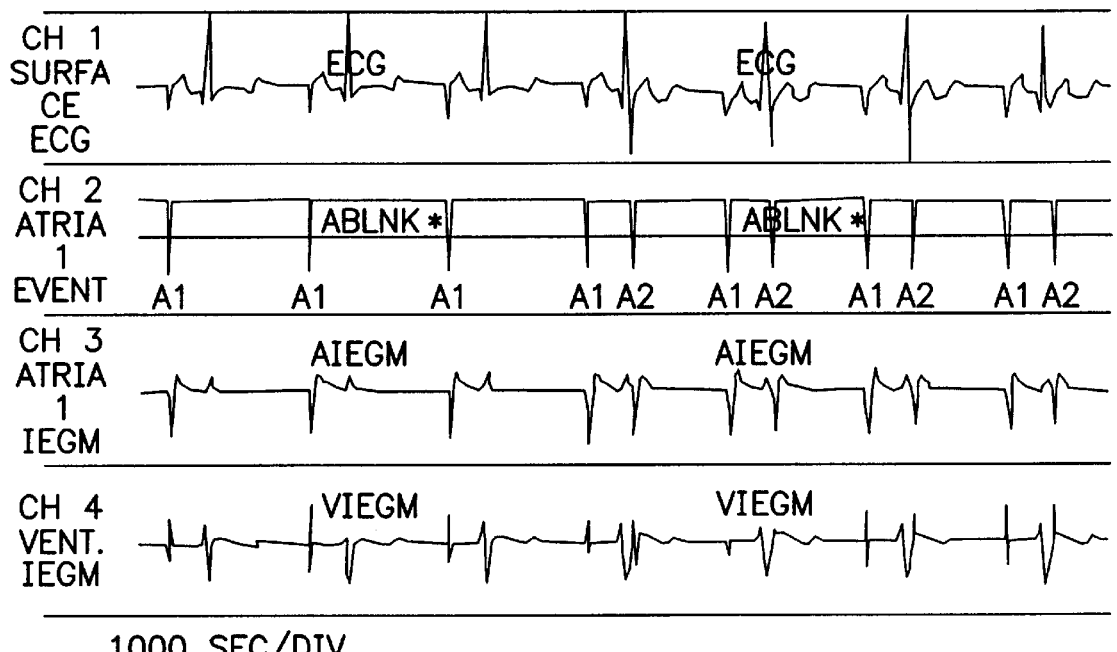
FIGS. 3 and 4 are cardiac electrograms that illustrate the affects of adjusting the delay between the primary and secondary atrial pulses.
Figure 4:
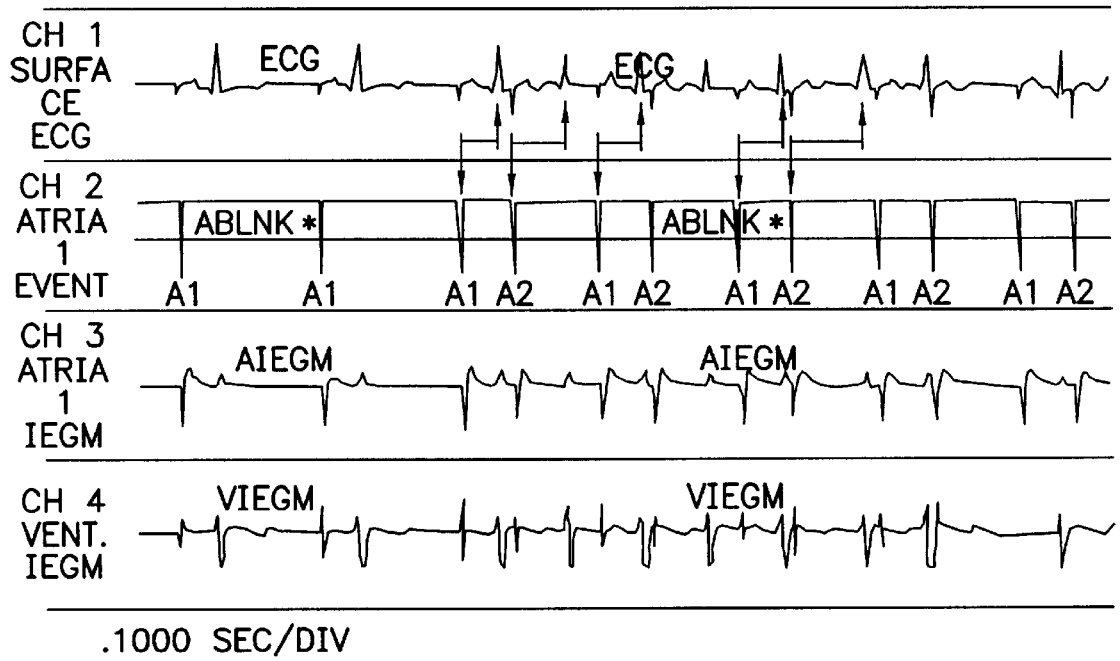

FIGS. 3 and 4 show examples of the use of the present invention. In the figures, A1 refers to a primary atrial pulse and A2 refers to a secondary atrial pulse. FIG. 3 shows surface ECG, atrial pacing event markers, atrial IEGM and ventricular IEGM during double atrial pacing in AOO mode at a base rate of 90 bpm with an A1–A2 delay of 220 ms. The subject was a dog under the influence of a beta blocking drug (esmolol) given to slow AV nodal conduction. Note that all atrial stimuli captured the atrium as indicated by evoked responses evident in the atrial IEGM. However, only the A1 initiated atrial depolarizations conducted to the ventricle. This is because the A2 initiated depolarization arrives at the AV node while it is still refractory due to conducting the A1 initiated depolarization.

FIG. 4 depicts the same conditions as FIG. 3 except that the A1–A2 interval is 260 ms. Note that all atrial stimuli captured the atrium. Note also that the first two and possibly the third A2-initiated atrial depolarizations conduct to the ventricle. This is because the AV node has had time to recover from conducting the A1 initiated depolarization and is no longer refractory when the A2 initiated depolarization arrives. AV nodal conduction is intermittent, with 6 out of 10 consecutive A2 stimuli conducting in the test that produced this figure.

Figure 5:
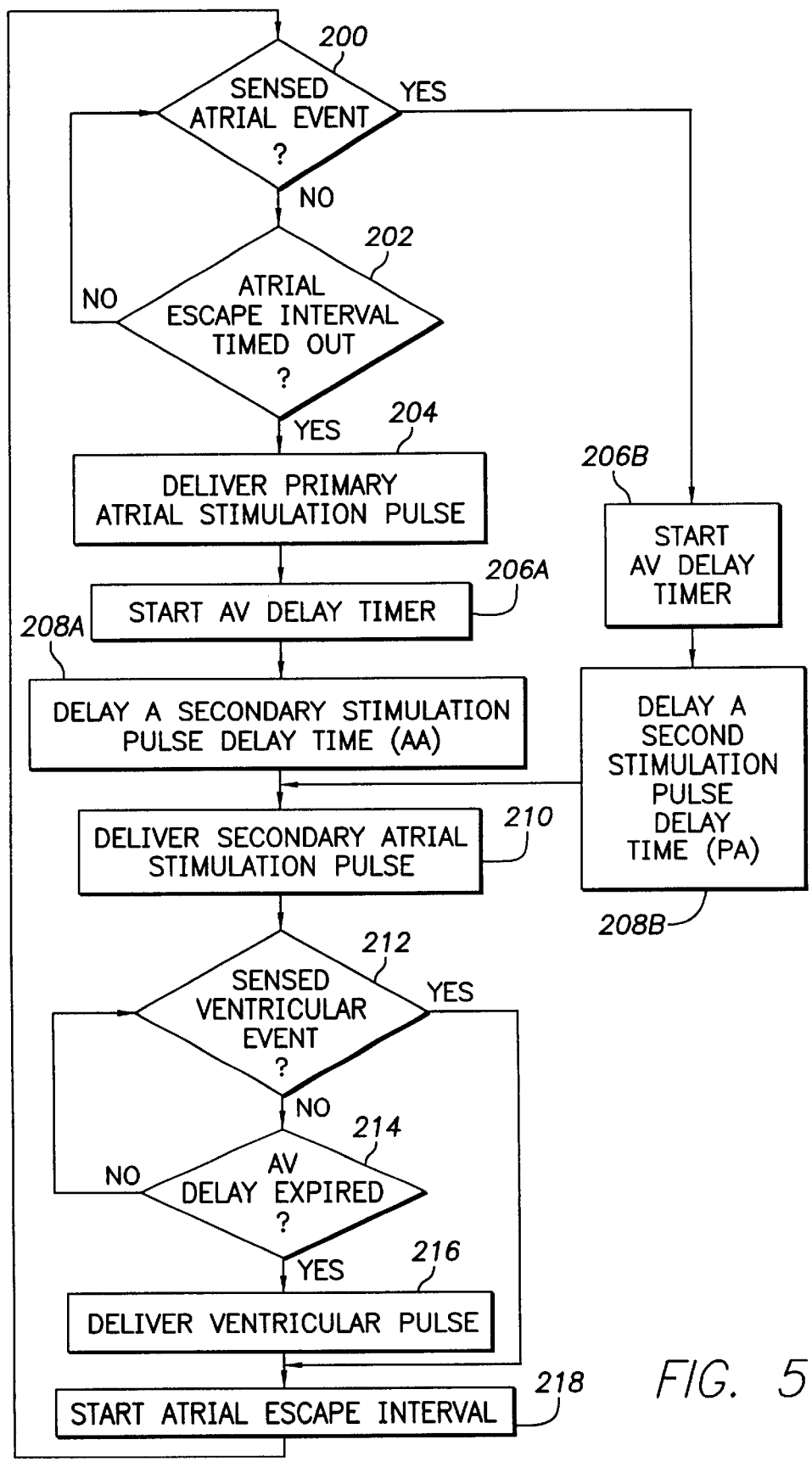
FIG. 5 is a simplified flowchart of an exemplary implementation of the method of the present invention.

FIG. 5 is a simplified flow chart showing an exemplary implementation of a dual chamber embodiment of the present invention showing the operation of the microprocessor 80 during each cardiac cycle. Initially in step 200, the atrial threshold sensor 56 is used to determine whether an atrial event has been sensed. If there has not yet been an atrial event, the microprocessor 80 determines in step 202 using atrial delay timer 94 whether the atrial escape interval has timed out. If the atrial escape interval has not timed out, the process continues with step 200. If the atrial escape interval has timed out, the process continues with the primary atrial pacing pulse stimulation control 88 causing the atrial pulse generator 72 to generate a primary atrial stimulation pulse in step 204. Next, the AV delay timer 96 is set in step 206A and a secondary stimulation pulse AA (atrial to atrial pulse) delay, e.g., 180 to 300 ms., is started in step 208A. Alternatively, step 206B is processed if an atrial event was sensed in step 200 and a secondary stimulation pulse PA (P-wave to atrial pulse) delay, e.g., 180 to 300 ms., is started in step 208B.

In either case, the process continues with step 210 if either (1) an intrinsic atrial event was sensed or (2) if a primary atrial stimulation pulse was delivered. In step 210, the secondary atrial pacing pulse stimulation control 90 causes the atrial pulse generator 72 to deliver a secondary atrial stimulation pulse following the time out of atrial delay timer 94. In step 212, it is determined whether a ventricular event, i.e., depolarization signifying activation of the ventricle, has occurred using the ventricular threshold sensor 66. If there has not been a ventricular event sensed, the process continues with step 214 which determines using AV delay timer 96 whether the AV delay has expired. If the AV delay has not expired, the process returns to step 212 to continue looking for a ventricular event. If the AV delay has expired, the ventricular pacing pulse stimulation control 92 causes the ventricular pulse generator 74 to deliver a ventricular pulse in step 216. The atrial escape interval is then started in step 218 and the process continues with step 200 for the next cardiac cycle. Alternatively, the atrial escape interval begins following detection of a ventricular event in step 212.

As has been discussed, the atrial refractory period can be extended by providing a secondary atrial pulse a delay time following either an intrinsic atrial event, i.e., a P-wave, or the delivery of a primary atrial pulse. However, the delay time must be within an appropriate range for each patient. If the delay time is too short, e.g., less than 120 to 150 ms., the secondary atrial pulse may cause atrial fibrillation. If the delay time is too long, e.g., greater than 300 ms., the AV node will no longer be in its refractory period and the ventricle may be stimulated. Accordingly, an exemplary auto-adjustment mode for determining optimal AA (primary atrial pulse to secondary atrial pulse) and PA (intrinsic P-wave to secondary atrial pulse) delay time values, is presented in reference to FIG. 6.

Figure 6:
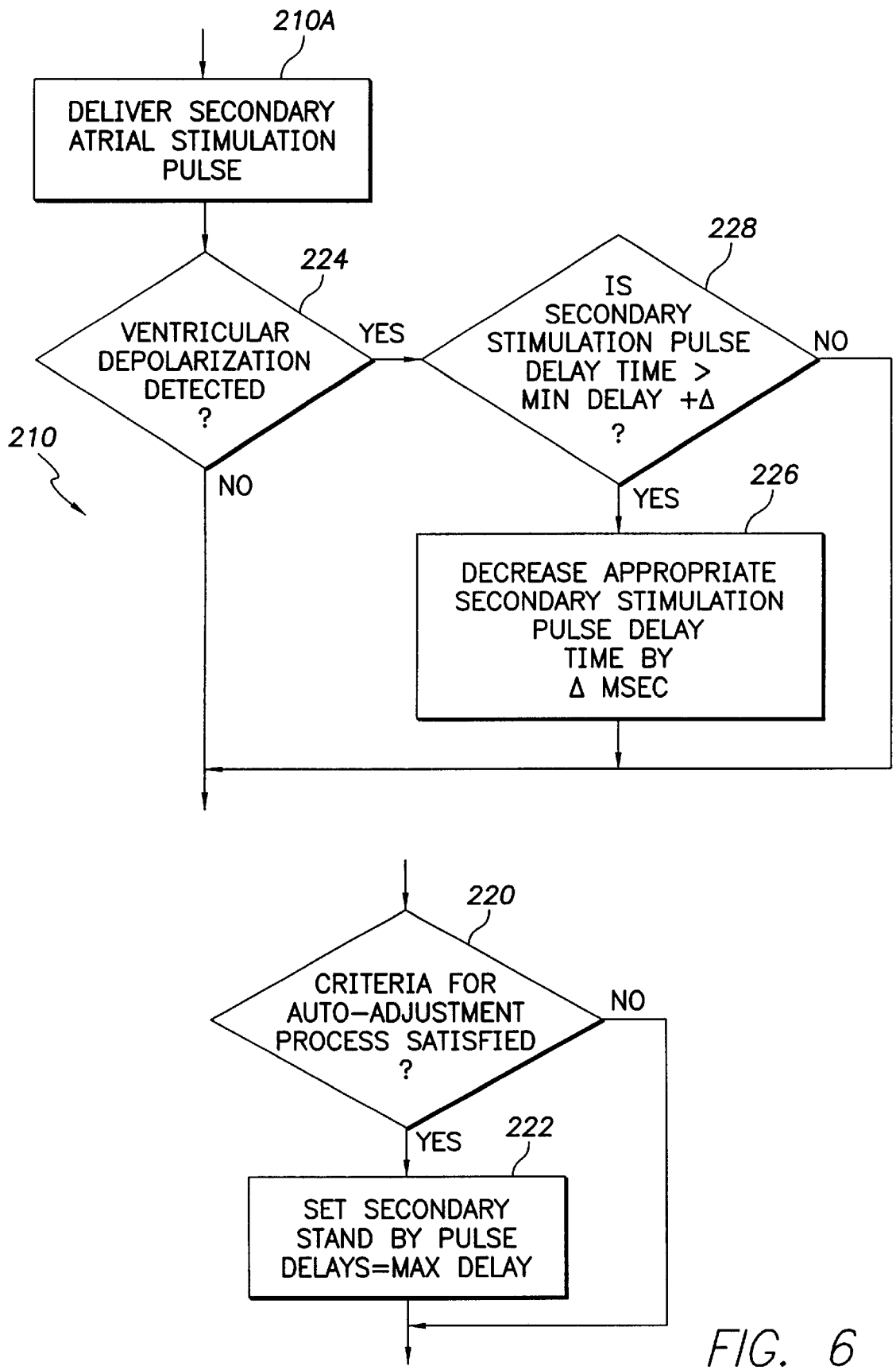
FIG. 6 is a simplified flowchart of an exemplary process for automatically adjusting the atrial delay time between a primary atrial event and delivery of the secondary atrial pacing pulse if a ventricular depolarization occurs in response to the secondary atrial pacing pulse.

Following, a predetermined time period (see step 220), e.g., once an hour to once a day, the AA and PA delay time values are extended to a MaxDelay value, e.g., 350 ms., (see step 222) to restart an auto-adjustment process. These delay time values are used in step 210 (see FIG. 5) to determine when the secondary atrial pulse should be delivered. However, as shown in FIG. 6, optimal delay time values are determined. Following the delivery of the secondary atrial pulse in step 210A, the microprocessor 80 determines in step 224 using the ventricular sense channel 62 whether a ventricular activation, i.e., depolarization occurred. If ventricular depolarization occurs, then the appropriate delay time value is decreased in step 226 by a predetermined amount Δ, e.g., 5 ms. The appropriate delay time value is selected by determining by whether the primary atrial event was either the delivery of a primary atrial pulse (in which case the AA delay time is decreased) or whether the primary atrial event was the detection of a P-wave (in which case the PA delay time is decreased). However, as previously discussed, the delay time values are not allowed to decrease below a MinDelay time, e.g., 120 to 150 ms. Accordingly, it is determined in step 228 whether current delay time value +Δ exceeds the MinDelay value. If this condition is not satisfied, step 226 is bypassed.

The present invention provides a therapy that can be advantageously used by an implantable cardiac stimulation device for prolonging atrial refractoriness to avoid the potential for atrial fibrillation and flutter. However, the use of multiple atrial pacing pulses will increase the battery consumption and thus limit the life of the implantable cardiac stimulation device. Accordingly, it may be desirable to restrict the use of the afore described therapy to periods of time when prolonging atrial refractoriness would be most beneficial to a patient. For example, when a patient is at rest there is greater tendency for vagal-mediated tachycardia to occur. Accordingly, it may be desirable to only enable secondary atrial pacing pulses during periods of rest. Such periods of rest can be determined as described in U.S. Pat. No. 5,476,483 to Bornzin, et al. which is incorporated herein by reference. Additionally, it may be desirable to sense the occurrence of a high incidence of PACs (premature atrial contractions), e.g., greater than 2 PACs per minute, and use this occurrence as a triggering event to enable secondary atrial pacing pulses. In an exemplary use, the previously described method of providing secondary atrial pacing pulses would be enabled for a predetermined period of time, e.g., an hour, following a high incidence of PACs. Following this predetermined period, secondary atrial pacing pulses would again be disabled. If a high incidence of PACs should reoccur, the therapy would again be enabled. Accordingly, battery consumption would be minimized by only providing this therapy when it is needed.

While the invention has been described by means of specific embodiments and applications thereof, it is understood that numerous modifications and variations could be made thereto by those skilled in the art without departing from the spirit and scope of the invention. For example, dual site atrial pacing in accordance with the present invention is also possible. Such dual site atrial pacing may be provided by a second atrial electrode pair being implanted in the coronary sinus near the left ventricular free wall or, during open heart surgery, being placed on the left atrial myocardium. The second atrial electrode pair may then be paced simultaneously with the atrial electrode pair implanted in the right atrium. It is therefore to be understood that within the scope of the claims, the invention may be practiced otherwise than as specifically described herein.

What is claimed is:

1. An implantable cardiac stimulation device for stimulating a patient's heart through a first electrode implanted in electrical contact with an atrium of the patient's heart, the cardiac stimulation device comprising:
    a first pulse generator adapted to be electrically coupled to the electrode and configured to generate stimulation pulses to thereby stimulate the patient's heart; and
    a controller coupled to the first pulse generator for causing the first pulse generator to deliver a secondary atrial pacing pulse to the atrium an atrial delay time after a primary atrial event, whereby the refractory period of the atrium is prolonged.

2. The implantable cardiac stimulation device of claim 1 further including an atrial detection circuit adapted to be coupled to the first electrode and configured to determine the presence of a P-wave as the primary atrial event wherein the secondary atrial pacing pulse is delivered a first determined atrial delay time after the P-wave.

3. The implantable cardiac stimulation device of claim 1 wherein the primary atrial event is the delivery of a primary atrial pacing pulse by the first pulse generator under control of the controller wherein the secondary atrial pacing pulse is delivered a second determined atrial delay time after the primary atrial pacing pulse.

4. The implantable cardiac stimulation device of claim 1 wherein the determined atrial delay time is between about 180 milliseconds and 300 milliseconds.

5. The implantable cardiac stimulation device of claim 1 wherein the cardiac stimulation device is additionally configured to stimulate a ventricle of the patient's heart through a second electrode implanted in electrical contact with a ventricle of the patient's heart, the cardiac stimulation device further including:
    an AV delay timer that times an AV delay interval, wherein the AV delay timer is responsive to the primary atrial event, and
    a second pulse generator responsive to the AV delay timer that provides a ventricular pacing pulse at the end of the AV delay interval.

6. The implantable cardiac stimulation device of claim 5 further including an atrial detection circuit adapted to be coupled to the first electrode and configured to determine the presence of a P-wave as the primary atrial event.

7. The implantable cardiac stimulation device of claim 5 wherein the primary atrial event is the delivery of a primary atrial pacing pulse by the first pulse generator under control of the controller.

8. The implantable cardiac stimulation device of claim 5, further comprising:
    a ventricular detection circuit that detects ventricular events; and whereby
    the controller inhibits the second pulse generator when a ventricular event is detected during the AV delay interval.

9. The implantable cardiac stimulation device of claim 5 further including an atrial delay timer for timing the atrial delay time.

10. The implantable cardiac stimulation device of claim 5 wherein the atrial delay time is between about 180 milliseconds and 300 milliseconds.

11. The implantable cardiac stimulation device of claim 1 wherein the atrial delay timer is additionally configured to time an atrial escape interval following a ventricular event and wherein the first pulse generator is configured to deliver a primary atrial pacing pulse at the end of the atrial escape interval.

12. The implantable cardiac stimulation device of claim 1 wherein the primary atrial event includes detection of a P-wave and delivery of a primary atrial pacing pulse and the atrial delay time includes a first determined delay time following the detection of a P-wave and a second atrial delay time following delivery of a primary atrial pacing pulse.

13. The implantable cardiac stimulation device of claim 1 wherein the atrial delay time is periodically determined to prolong the refractory period of the atrium while avoiding stimulation of the ventricle of the patient's heart resulting from the secondary atrial pacing pulse.

14. The implantable cardiac stimulation device of claim 1 wherein the delivery of the secondary atrial pacing pulse is limited to predefined time periods.

15. The implantable cardiac stimulation device of claim 14 wherein the predefined time periods include those time periods when the patient is at rest.

16. The implantable cardiac stimulation device of claim 14 wherein the predefined time periods include a period of time following detection of a high incidence of premature atrial contractions.

17. An implantable cardiac stimulation device comprising:
    generating means for delivering pacing pulses to an atrium of a patient's heart; and
    control means coupled to the generating means for causing the generating means to deliver a primary pacing pulse to the atrium and causing the generating means to deliver a secondary pacing pulse to the atrium a delay time after the delivery of the primary pacing pulse.

18. The implantable cardiac stimulation device of claim 17 further including:
    AV delay timing means for timing an AV delay interval responsive to the delivery of a primary pacing pulse; and
    second generating means responsive to the AV delay timing means for providing a ventricular pacing pulse at the end of the AV delay interval.

19. The implantable cardiac stimulation device of claim 18 further including ventricular activation detecting means for detecting ventricular activations of the heart and ventricular inhibiting means for inhibiting the second generating means when a ventricular activation is detected during the AV delay interval.

20. The implantable cardiac stimulation device of claim 17 further including timing means for timing the delay time.

21. The implantable cardiac stimulation device of claim 20 wherein the delay time is between about 180 milliseconds and 300 milliseconds.

22. The implantable cardiac stimulation device of claim 17 further including detecting means for detecting atrial activations of the heart, wherein the control means includes inhibiting means for inhibiting the generator from providing the primary pacing pulse when an atrial activation is detected during an escape interval and wherein the control means further causes the generator to deliver the secondary pacing pulse to the atrium the delay time after an atrial activation is detected during the escape interval.

23. The implantable cardiac stimulation device of claim 22 further including a timing means for timing the delay time responsive to the delivery of a primary pacing pulse or the detection of an atrial activation during the escape interval.

24. The implantable cardiac stimulation device of claim 23 wherein the delay time is between about 180 milliseconds and 300 milliseconds.

25. The implantable cardiac stimulation device of claim 22 further including AV delay timing means for timing an AV delay interval responsive to the delivery of a primary pacing pulse or the detection of an atrial activation within the escape interval; and second generating means responsive to the AV delay timing means for providing a ventricular pacing pulse at the end of the AV delay interval.

26. The implantable cardiac stimulation device of claim 25 further including ventricular activation detecting means for detecting ventricular activations of the heart and ventricular inhibiting means for inhibiting the second generating means when a ventricular activation is detected during the AV delay interval.

27. The implantable cardiac stimulation device of claim 17 wherein the delivery of the secondary atrial pacing pulse is limited to predefined time periods.

28. The implantable cardiac stimulation device of claim 27 wherein the predefined time periods include those time periods when the patient is at rest.

29. The implantable cardiac stimulation device of claim 27 wherein the predefined time periods include a period of time following detection of a high incidence of premature atrial contractions.

30. A method of pacing a patient's heart, the method comprising the steps of:
   determining a primary atrial event;
   timing a delay time period following the primary atrial event; and
   delivering a secondary atrial pacing pulse to an atrium of the patient's heart at the end of the delay time period, whereby the refractory period of the atrium is prolonged.

31. The method of claim 30 wherein the delay time period is between about 180 milliseconds and 300 milliseconds.

32. The method of claim 30 additionally comprising the step of detecting the presence of a P-wave and designating the detected P-wave as the primary atrial event.

33. The method of claim 30 additionally comprising delivering a primary pacing pulse to the atrium of the patients heart, wherein the primary atrial pacing pulse is designated as the primary atrial event.

34. The method of claim 30 additionally comprising the step of timing an AV delay time period following the primary atrial event and delivering a ventricular pacing pulse to a ventricle of the patient's heart at the end of the AV delay time period.

35. The method of claim 34 additionally comprising the step of detecting ventricular activations of the patient's heart and inhibiting the delivery of the ventricular pacing pulse to the ventricle when a ventricular event is detected during the AV delay time period.

36. The method of claim 30 additionally comprising the steps of:
   detecting atrial activations of the patient's heart;
   timing an atrial escape interval;
   inhibiting the delivery of the primary atrial pacing pulse when an atrial activation is detected during the atrial escape interval; and
   timing the delay time period upon detecting an atrial activation during the atrial escape interval.

37. The method of claim 30 additionally comprising the steps of:
   setting the delay time period to a predetermined maximum value;
   sensing, following the delivery of each secondary atrial pacing pulse, whether a ventricular depolarization occurred; and
   decreasing the delay time period by a predetermined amount if a ventricular depolarization was sensed in response to the secondary atrial pacing pulse.

38. The method of claim 37 wherein the step of decreasing the delay time period is bypassed if the decreasing step would decrease the delay time below a predetermined minimum value.

39. The method of claim 37 wherein the step of setting the delay time period to a predetermined maximum value occurs periodically.

40. The method of claim 30 wherein the step of delivering the secondary atrial pacing pulse is limited to predefined time periods.

41. The method of claim 40 wherein the predefined time periods include those time periods when the patient is at rest.

42. The method of claim 40 wherein the predefined time periods include a period of time following detection of a high incidence of premature atrial contractions.

43. An implantable cardiac stimulation device for stimulating a patient's heart through a first electrode in electrical communication with an atrium of the patient's heart, the implantable stimulation device comprising:
   a pulse generator adapted to be electrically coupled to the electrode and that is operative to generate pacing pulses for delivery to the atrium via the electrode; and
   a controller that is coupled to the pulse generator and operative to cause the pulse generator to deliver a primary pacing pulse to the atrium and a secondary pacing pulse to the atrium a delay time after the delivery of the primary pacing pulse.

44. The implantable cardiac stimulation device of claim 43 wherein the delay time is at least about 120 milliseconds.

45. The implantable cardiac stimulation device of claim 44 wherein the delay time is between about 180 milliseconds and 300 milliseconds.

46. An implantable cardiac stimulation device for stimulating a patient's heart through a first electrode in electrical communication with an atrium of the patient's heart, the implantable stimulation device comprising:

sensing circuitry that senses cardiac activity;

a pulse generator adapted to be electrically coupled to the electrode and that is operative to generate pacing pulses for delivery to the atrium via the electrode; and a controller that is coupled to the sensing circuitry and the pulse generator, wherein the controller is operative to receive sense signals from the sensing circuitry and to cause the pulse generator to deliver a secondary pacing pulse to the atrium at least about 120 milliseconds after a primary atrial event.

47. The implantable cardiac stimulation device of claim 46 wherein the atrial delay time is at least about 150 milliseconds.

48. The implantable cardiac stimulation device of claim 46 wherein the atrial delay time is between about 180 milliseconds and 300 milliseconds.

49. The implantable cardiac stimulation device of claim 46 wherein the primary atrial event is a primary pacing pulse, and wherein the controller is responsive to the detection of no intrinsic activity after an escape interval to control the pulse generator to deliver the primary pacing pulse.

\* \* \* \* \*